US006576762B2

(12) United States Patent
Hoffmann et al.

(10) Patent No.: US 6,576,762 B2
(45) Date of Patent: Jun. 10, 2003

(54) HETEROAROMATIC SUBSTITUTED AMIDES WITH ANTAGONISTIC ACTIVITY TO NEUROKININ 1 RECEPTORS

(75) Inventors: Torsten Hoffmann, Weil am Rhein (DE); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/901,311

(22) Filed: Jul. 9, 2001

(65) Prior Publication Data

US 2002/0038030 A1 Mar. 28, 2002

(30) Foreign Application Priority Data

Jul. 24, 2000 (EP) ............................................. 00115846

(51) Int. Cl.[7] ............................................. C07D 265/28
(52) U.S. Cl. ................... 544/98; 546/272.4; 546/274.1; 546/275.4; 546/194; 546/309; 514/228.8; 514/318; 514/340; 514/341; 514/349
(58) Field of Search ................................ 546/309, 194, 546/275.4, 272.4, 274.1; 544/98; 514/318, 349, 341, 340, 228.8

(56) References Cited

U.S. PATENT DOCUMENTS

| 5,972,938 A | 10/1999 | Rupniak et al. ......... 514/236.2 |
| 6,225,316 B1 * | 5/2001 | Bos et al. ................... 514/334 |
| 6,297,375 B1 | 10/2001 | Bos et al. |

FOREIGN PATENT DOCUMENTS

| DE | 10008042 | 8/2000 |
| WO | 95/16679 | 6/1995 |
| WO | WO 99/47132 | 6/1995 |
| WO | 95/18124 | 7/1995 |
| WO | 95/23798 | 9/1995 |

OTHER PUBLICATIONS

Ikeura et al., *Chem. Pharm. Bull.*, vol. 45, No. 10, pp. 1642–1652 (1997).
Natsugari et al., *J. Med. Chem.*, vol. 38, No. 16, pp. 3106–3120 (1995).
Hosoki et al., *Eur. J. of Pharma.*, vol. 341, No. 2/3, pp. 235–241 (1998).
Barker, *reviews in the Neurosciences*, vol. 7,, No. 3, pp. 187–214 (1996).
Longmore et al., *Can. J. Physiol. Pharmacol.*, vol. 75, pp. 612–621 (1997).
Kramer et al., *Science*, vol. 281,pp.1640–1645.
Maggi et al.,*J. Auton. Pharmacol*, vol. 13, pp. 23–93 (1993).
Navari et al., *The New England Journal of Medicine*, vol.340, No. 3, pp. 190–195 (1999).
Neuropeptides, vol. 32(1), pp. 1–49 (1998).
Eur. J. Pharmacol., vol. 383(3), pp. 297–303 (1999).

* cited by examiner

*Primary Examiner*—Jane T. Fan
(74) *Attorney, Agent, or Firm*—George W. Johnston; Patricia S. Rocha-Tramaloni; Kimberly J. Prior

(57) ABSTRACT

The present invention is a heteroaromatic substituted amide showing antagonist activity to neurokinin 1 (NK-1, substance P) receptors.

3 Claims, No Drawings

HETEROAROMATIC SUBSTITUTED AMIDES WITH ANTAGONISTIC ACTIVITY TO NEUROKININ 1 RECEPTORS

FIELD OF INVENTION

The present invention is generally related to novel heteroaromatic substituted amide compounds and more particularly to heteroaromatic substituted amide compounds showing antagonist activity to neurokinin 1 (NK-1, substance P) receptors.

BACKGROUND

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes. The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

"Tachykinin Receptor and Tachykinin Receptor Antagonists", J. Auton. Pharmacol., 13, 23–93, 1993 reviews evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases. The neurokinin-1 receptor antagonists are also known to be useful for the treatment of motion sickness and for treatment of induced vomiting.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

In addition, a paper published in The New England Journal of Medicine, Vol. 340, No. 3 190–195, 1999 describes the reduction of cisplatin-induced emesis by a selective neurokinin-1-receptor antagonist.

U.S. Pat. No. 5,972,938 discloses a method for treating a psychoimmunologic or a psychosomatic disorder by administration of a tachykinin receptor, such as NK-1 receptor antagonist.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

A 4-phenyl-pyridine compound, related to compounds disclosed in the present application, is disclosed in U.S. app. Ser. No. 09/507,456 (EP 1,035,115).

SUMMARY

The present invention relates to compounds having the formulae

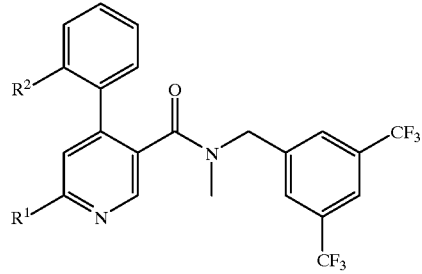

IA or

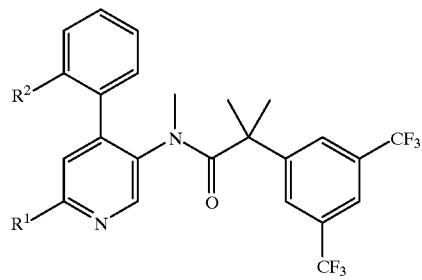

IB wherein
R$^1$ is

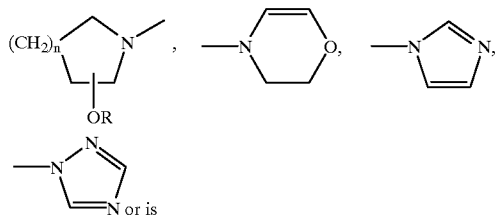

—NH(CH$_2$)$_2$OH or —NR$^3$C(O)R$^4$;

R$^2$ is methyl or chloro;
R$^3$ is hydrogen or methyl;
R$^4$ is lower alkyl or lower cycloalkyl;
R is hydrogen or —(CH$_2$)$_2$OH; and
n is 1 or 2
or a pharmaceutically acceptable acid addition salt thereof.

The compounds of formulae IA and IB can also be used in form of their prodrugs. Examples are esters, N-oxides, phosphate esters, glycoamide esters, glyceride conjugates and the like. The prodrugs may add to the value of the present compound's advantages in adsorption, pharmacokinetics in distribution and transport to the brain.

The compounds of formulae IA and IB and their salts are characterized by valuable therapeutic properties. It has been surprisingly found that the compounds of the present invention are antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors therefore, the compounds of the invention can be used to treat diseases associated with an excess or imbalance of tachykinin, in particular substance P. Examples of conditions in which substance P has been implicated include disorders of the central nervous system such as anxiety, depression and psychosis.

DETAILED DESCRIPTION

The following definitions of the general terms used in the present description apply irrespective of whether the terms in question appear alone or in combination. As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like. Preferred lower alkyl groups are groups with 1–4 carbon atoms. Particularly preferred are methyl groups. The term "cycloalkyl" denotes a saturated carbocyclic group, containing 3–6 carbon atoms. A preferred cycloalkyl group is cyclopropyl.

Exemplary preferred are compounds of formula IA, in which $R^2$ is methyl, for example the following compounds:
N-(3,5-bis-trifluoromethyl-benzyl)-N-methyl-4-o-tolyl-6-[1,2,4]triazol-1-yl-nicotinamide,
N-(3,5-bis-trifluoromethyl-benzyl)-6-(2-hydroxy-ethylamino)-N-methyl-4-o-tolyl-nicotinamide,
4-hydroxy-4'-o-tolyl-3,4,5,6-tetrahydro-2H-[1,2']bipyridinyl-5'-carboxylic acid (3,5-bis-trifluoromethyl-benzyl)-methyl-amide,
4-(2-hydroxy-ethoxy)-4'-o-tolyl-3,4,5,6-tetrahydro-2H-[1,2']bipyridinyl-5'-carboxylic acid (3,5-bis-trifluoromethyl-benzyl)-methyl-amide or
(R)-N-(3,5-bis-trifluoromethyl-benzyl)-6-(3-hydroxy-pyrrolidin-1-yl)-N-methyl-4-o-tolyl-nicotinamide.

Further preferred are compounds of formula IA, in which $R^2$ is chloro.

An example of such compound is:
4'-(2-chloro-phenyl)-4-hydroxy-3,4,5,6-tetrahydro-2H-[1,2']bipyridinyl-5'-carboxylic acid (3,5-bis-trifluoromethyl-benzyl)-methyl-amide Exemplary preferred are compounds of formula IB, in which $R^2$ is methyl, for example the following compounds:
2-(3,5-bis-trifluoromethyl-phenyl)-N-[6-(2-hydroxy-ethylamino)-4-o-tolyl-pyridin-3-yl]-N-methyl-isobutyramide,
2-(3,5-bis-trifluoromethyl-phenyl)-N-[6-(2,3-dihydro-[1,4]oxazin-4-yl)-4-o-tolyl-pyridin-3-yl]-N-methyl-isobutyramide,
N-(6-acetylamino-4-o-tolyl-pyridin-3-yl)-2-(3,5-bis-trifluoromethyl-phenyl)-N-methyl-isobutyramide,
N-[6-(acetyl-methyl-amino)-4-o-tolyl-pyridin-3-yl]-2-(3,5-bis-trifluoromethyl-phenyl)-N-methyl-isobutyram cyclopropanecarboxylic acid (5-{[2-(3,5-bis-trifluoromethyl-phenyl)-2-methyl-propionyl]-methyl-amino}-4-o-tolyl-pyridin-2-yl)-amide,
cyclopropanecarboxylic acid (5-{[2-(3,5-bis-trifluoromethyl-phenyl)-2-methyl-propionyl]-methyl-amino}-4-o-tolyl-pyridin-2-yl)-methyl-amide or
2-(3,5-bis-trifluoromethyl-phenyl)-N-(6-imidazol-1-yl-4-o-tolyl-pyridin-3-yl)-N-methyl-isobutyramide.

Further preferred are compounds of formula IB, in which $R^2$ is chloro, for example the following compound:
2-(3,5-bis-trifluoromethyl-phenyl)-N-[4-(2-chloro-phenyl)-6-(2-hydroxy-ethylamino)-pyridin-3-yl]-N-methyl-isobutyramide.

Also preferred are compounds of formula 1B, in which $R^1$ is —NH(CH)$_2$OH. Also for formula 1B, $R^1$ is preferred as —NR$^3$C(O)R$^4$, $R^3$ is methyl and $R^4$ is lower alkyl. $R^4$ being methyl is particularly preferred. Additionally, $R^4$ is preferred as cycloalkyl, particularly cyclopropyl. Additionally, for formula 1B, $R^1$ is preferred as a heterocycle, with oxazine and imidazole being preferred heterocycles when $R^2$ is methyl.

The present compounds of formulae IA and IB and their pharmaceutically acceptable salts can be prepared by methods known in the art, for example, by processes described below, which process comprises reacting a compound of formula

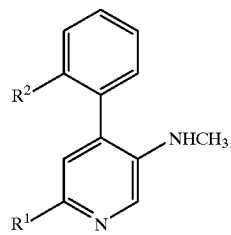

II with a compound of formula

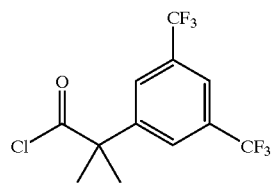

III to a compound of formula

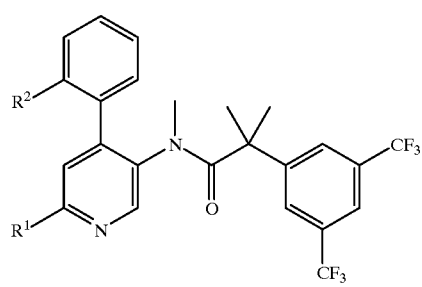

IB wherein $R^1$ and $R^2$ have the significances given above, or
reacting a compound of formula

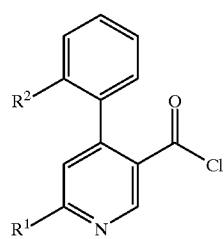

IV with a compound of formula

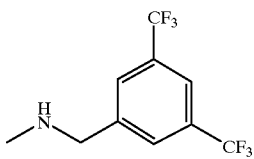

V to give a compound of formula

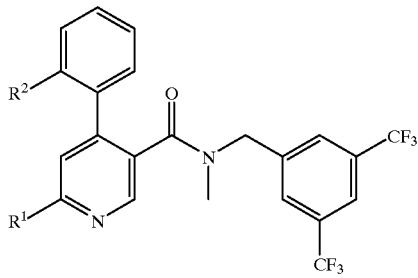

IA wherein R¹ and R² have the significances given above, or reacting a compound of formula

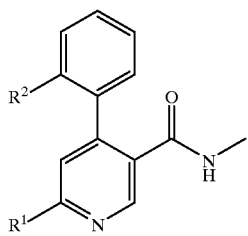

VI with a compound of formula

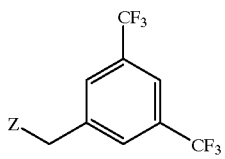

VII to a compound of formula

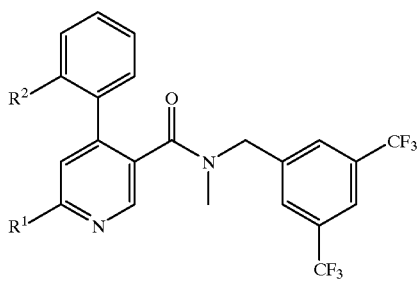

IA wherein Z is Cl, Br, I, —OS(O)$_2$C$_6$H$_4$CH$_3$ or —OS(O)$_2$CH$_3$ and the other definitions of substituents are given above, or reacting a compound of formula

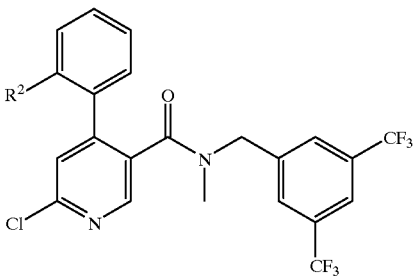

VIII or

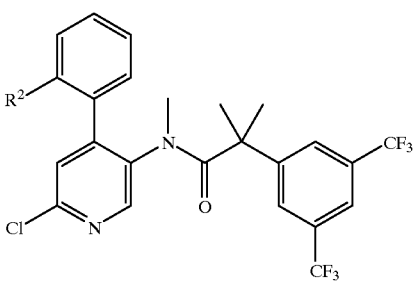

IX with a compound of formula

R¹H   XIV to a compound of formulae

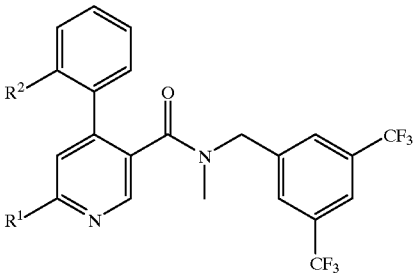

IA or

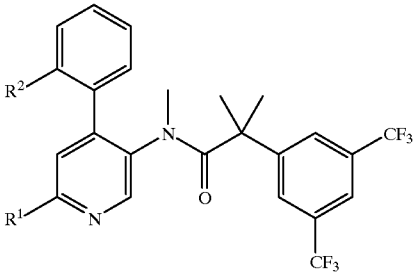

IB wherein the definition of substituents is given above, and if desired, converting the compound obtained into a pharmaceutically acceptable acid addition salt.

In accordance with process variant a) DIPEA (N-ethyldiisopropyl-amine) is added to a mixture of a compound of formula II and a compound of formula III in dichloromethane and the mixture is stirred at temperatures between 35–40° C. The desired compound of formula IB is isolated after purification in good yields.

Process variant b) describes the reaction of a compound of formula IV with a compound of formula V to a compound of formula IA. The reaction is carried out in conventional manner, for example in a solvent, such as a mixture of toluene and triethylamine. The mixture is refluxed for about 1 hour.

Process variant c) describes the reaction of a compound of formula VI with a compound of formula VII to a compound of formula IA. This reaction is carried out by deprotonation of a compound of formula VI with KHMDS (potassium hexamethyldisilazide) and subsequent addition of a compound of formula VII. A suitable solvent is tetrahydrofuran. The reaction is carried out at room temperature.

A further method for the preparation of a compound of formula IA or IB is described in process variant d). A compound of formulae VIII or IX is treated with a compound of formula XIV, which is, for example, 1,2,4-triazole, ethanolamine, 4-hydroxypiperidine, (R)-3-pyrrolidinol or morpholine. The reaction is carried out in THF, usually at 80–140° C.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–3 describe the processes for preparation of compounds of formulae IA and IB in more detail. The starting materials are known compounds or may be prepared according to methods known in the art.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |
| KHMDS | potassium hexamethyldisilazide |

Scheme 1

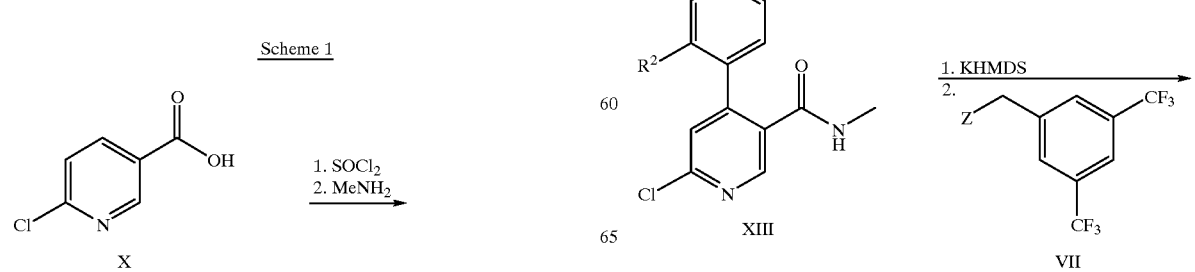

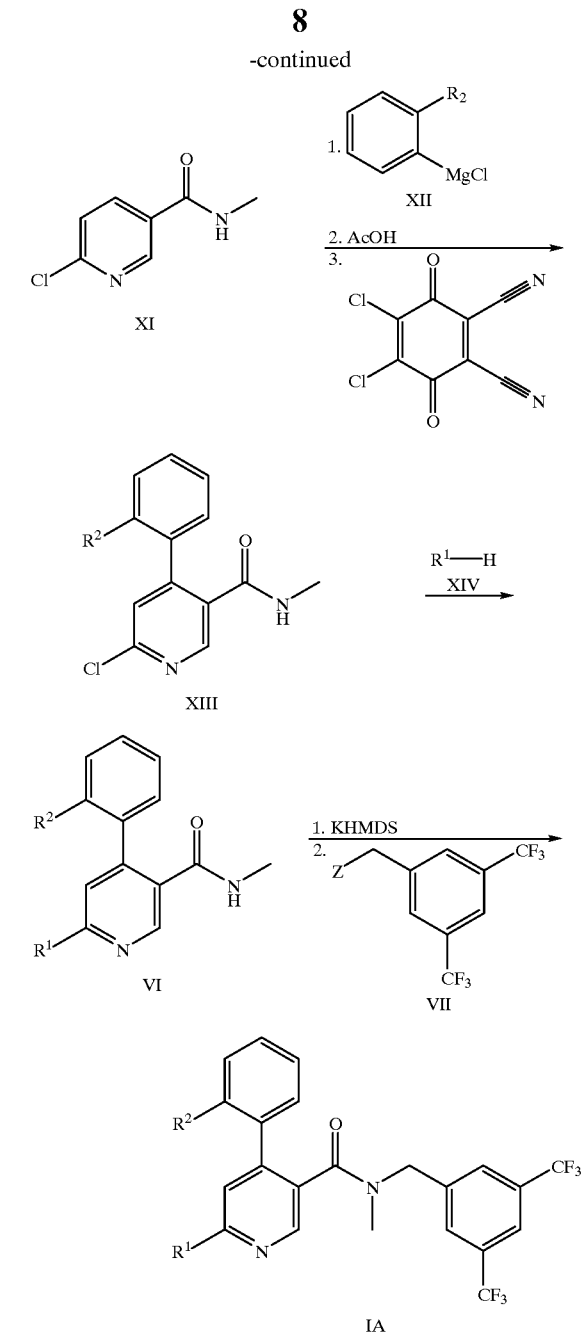

The definition of substituents is described above.

Scheme 2

-continued

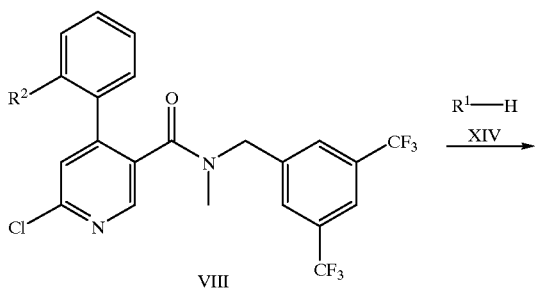

VIII

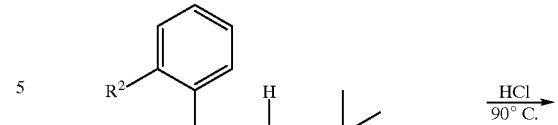

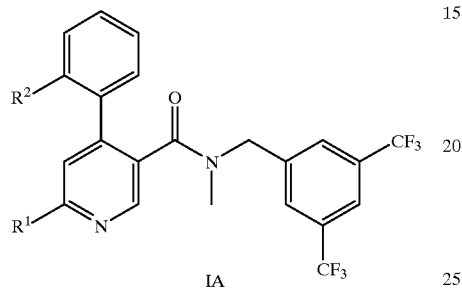

IA

The definition of substituents is described above.

Scheme 3

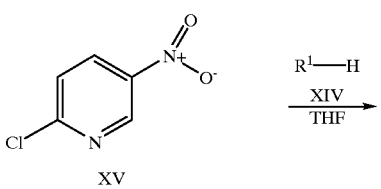

XV

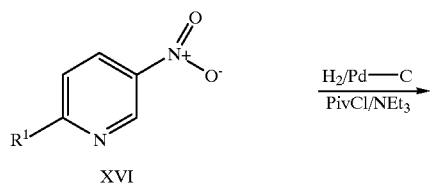

XVI

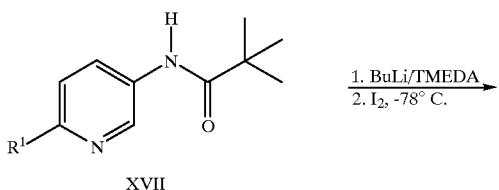

XVII

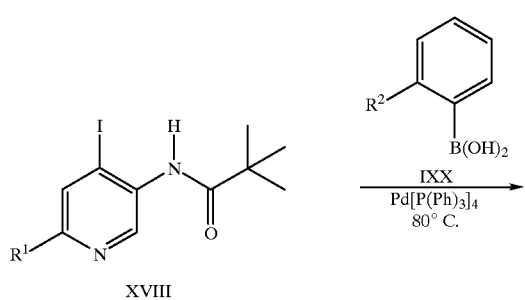

XVIII

-continued

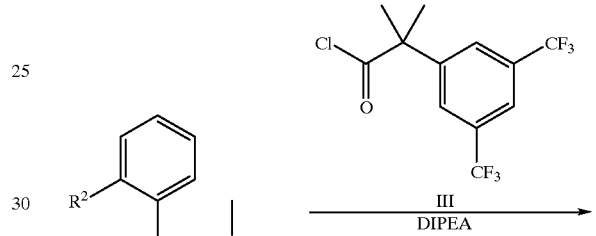

XX

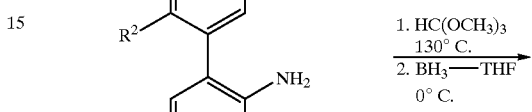

XXI

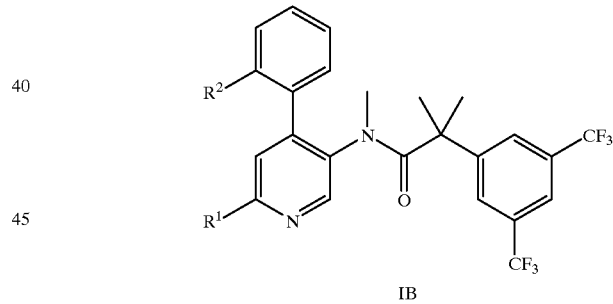

II

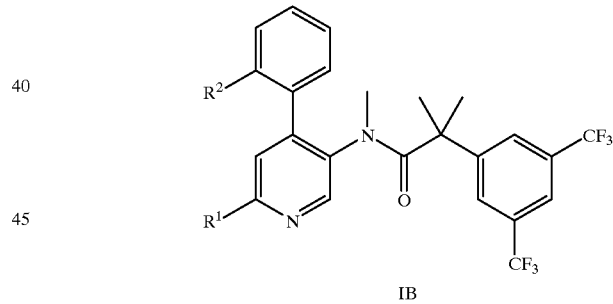

IB

The definition of substituents is described above.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

As mentioned earlier, the compounds of formulae IA and IB and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04 %) leupeptin (8 µg/ml), $MnCl_2$ (3 mM) and phosphoramidon (2 µM). Binding assays consisted of 250 µl of membrane suspension (1.25×10$^5$ cells/assay tube), 0.125 µl of buffer of displacing agent and 125 µl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.40–9.24 for the described exemplary compounds of the present invention.

| pKi | R$^1$ | R$^2$ | Formula | Expl. |
|---|---|---|---|---|
| 8.4 | 1,2,4-triazol-1-yl | CH$_3$ | IA | 1 |
| 8.87 | —NH(CH$_2$)$_2$OH | CH$_3$ | IA | 2 |
| 8.91 | 4-hydroxypiperidin-1-yl | CH$_3$ | IA | 3 |
| 9.03 | 4-(2-hydroxyethoxy)piperidin-1-yl | CH$_3$ | IA | 4 |
| 9.24 | 3-hydroxypyrrolidin-1-yl | CH$_3$ | IA | 5 |
| 9.18 | 4-hydroxypiperidin-1-yl | Cl | IA | 6 |
| 9.16 | —NH(CH$_2$)$_2$OH | CH$_3$ | IB | 7 |
| 9.14 | —NH(CH$_2$)$_2$OH | Cl | IB | 8 |
| 8.83 | morpholin-4-yl | CH$_3$ | IB | 9 |
| 8.6 | —NHC(O)CH$_3$ | CH$_3$ | IB | 10 |
| 8.71 | —N(CH$_3$)C(O)CH$_3$ | CH$_3$ | IB | 11 |
| 8.65 | —NH—C(O)-cyclopropyl | CH$_3$ | IB | 12 |
| 8.87 | —N(CH$_3$)—C(O)-cyclopropyl | CH$_3$ | IB | 13 |
| 8.65 | pyrazol-1-yl | CH$_3$ | IB | 14 |

The compounds the present invention of formulae IA and IB as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formulae IA and IB and their pharmaceutically usable acid addition salts can be processed with pharmaceutically inert, inorganic or organic excipients for the production of tablets, coated tablets, dragees and hard gelatine capsules. Lactose, cornstarch or derivatives thereof, talc, stearic acid or its salts etc. can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following Examples illustrate the present invention without limiting it. All temperatures are given in degrees Celsius.

EXAMPLE 1

N-(3,5-Bis-trifluoromethyl-benzyl)-N-methyl-4-o-tolyl-6-[1,2,4]triazol-1-yl-nicotinamide a) 6-Chloro-N-methyl-nicotinamide To 50 g (317 mmol) of 2-chloronicotinic acid was added 230 ml (3.16 mol) thionyl chloride at 0° C. After heating the mixture at reflux for 2 h excess thionyl chloride was removed by distillation. The oily brown residue was dissolved in 250 ml dichloromethane. The solution was treated with methylamine gas at 0° C. until no exothermic reaction was observed any longer. The resulting suspension was diluted with 1000 ml dichloromethane/water. The layers were separated and the aqueous layer extracted with three 300 ml portions of dichloromethane. Drying of the organic layer with sodium sulfate and concentration gave 53.2 g (98%) of the title compound as a light yellow solid.

MS m/e (%): 171 (M+H$^+$, 15).

b) 6-Chloro-N-methyl-4-o-tolyl-nicotinamide

To a solution of 3.41 g (20.0 mmol) 6-chloro-N-methyl-nicotinamide in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic layer washed with 4 250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid.

MS m/e (%): 260 (M$^+$, 11). M.p. 91–93° C.

c) N-(3,5-Bis-trifluoromethyl-benzyl)-6-chloro-N-methyl-4-o-tolyl-nicotinamide

To a solution of 10.0 g (38.4 mmol) 6-chloro-N-methyl-4-o-tolyl-nicotinamide in 190 ml tetrahydrofuran 46 ml of a 1 M solution (46 mmol) of potassium hexamethyldisilazide in tetrahydrofuran were added at 0° C. After 30 min, 8.5 ml (46 mmol) 3,5-bis(trifluoromethyl)benzyl bromide were added dropwise to the resulting suspension. After completed addition the ice-water cooling bath was removed and the reaction mixture was allowed to warm to room temperature. After 2 h the reaction was quenched with water. The mixture was adjusted to pH 3 with 1 M aqueous hydrochloric acid solution and stirred for 10 min. Basification with 1 M aqueous sodium hydroxide solution to pH 8 was followed by concentration to remove tetrahydrofuran. The aqueous residue was extracted with four portions of dichloromethane. The combined organic extracts were dried with sodium sulfate and concentrated to give 21.4 g of crude product. Column chromatography afforded 18.4 g (98.5%) of the title compound as a white solid.

MS m/e (%): 485 ([M-H]$^+$, 2).

d) N-(3,5-Bis-trifluoromethyl-benzyl)-N-methyl-4-o-tolyl-6-[1,2,4]triazol-1-yl-nicotinamide A mixture of 1.00 g (2.05 mmol) N-(3,5-bis-trifluoromethyl-benzyl)-6-chloro-N-methyl-4-o-tolyl-nicotinamide and 1.42 g (20.5 mmol) 1,2,4-triazole was stirred at 130° C. for 36 h. After cooling to room temperature the crude mixture was purified by flash chromatography to give 0.93 g (87%) of the title compound as a white solid.

MS m/e (%): 520 (M+H$^+$, 100).

EXAMPLE 2

N-(3,5-Bis-trifluoromethyl-benzyl)-6-(2-hydroxy-ethylamino)-N-methyl-4-o-tolyl-nicotinamide A mixture of 0.837 g (1.72 mmol) N-(3,5-bis-trifluoromethyl-benzyl)-6-chloro-N-methyl-4-o-tolyl-nicotinamide and 5.0 ml (83 mmol) ethanolamine was stirred at 100° C. for 48 h. After cooling to room temperature excess ethanolamine was removed under reduced pressure. The residue was dissolved in a mixture of ethyl acetate and saturated aqueous sodium bicarbonate solution. The layers were separated and the aqueous layer was extracted with two portions of ethyl acetate. The combined organic extracts were washed with saturated aqueous sodium bicarbonate solution and water, dried with sodium sulfate and concentrated to give 0.8 g of crude product. Flash chromatography afforded 0.650 g (73.9%) of the title compound as a white solid.

MS m/e (%): 512 (M+H$^+$, 100).

EXAMPLE 3

4-Hydroxy-4'-o-tolyl-3,4,5,6-tetrahydro-2H-[1,2']bipyridinyl-5'-carboxylic acid (3,5-bis-trifluoromethyl-benzyl)-methyl-amide A mixture of 10.0 g (20.5 mmol) N-(3,5-bis-trifluoromethyl-benzyl)-6-chloro-N-methyl-4-o-tolyl-nicotinamide, 3.1 g (31 mmol) 4-hydroxypiperidine, 10.6 ml (62 mmol) N-ethyldiisopropylamine and 0.13 g (1.0 mmol) 4-(N,N-dimethylamino)-pyridine was stirred at 140° C. for 70 h. After cooling to room temperature the residue was dissolved in a mixture of dichloromethane and water. The layers were separated and the aqueous layer was extracted with four portions of dichloromethane. The combined organic extracts were dried with sodium sulfate and concentrated to give 11.1 g of crude product. Flash chromatography afforded 9.0 g (80%) of the title compound as a white solid.

MS m/e (%): 552 (M+H$^+$, 100), M.p. 150–152° C.

EXAMPLE 4

4-(2-Hydroxy-ethoxy)-4'-o-tolyl-3,4,5,6-tetrahydro-2H-[1,2']bipyridinyl-5'-carboxylic acid (3,5-bis-trifluoromethyl-benzyl)-methyl-amide a) 4-[2-(tert-Butyl-dimethyl-silanyloxy)-ethoxy]-4'-o-tolyl-3,4,5,6-tetrahydro-2H-[1,2']bipyridinyl-5'-carboxylic acid (3,5-bis-trifluoromethyl-benzyl)-methyl-amide To a suspension of 48 mg (1.1 mmol) sodium hydride (55% in oil) and 17 mg (0.045 mmol) tetrabutylammonium iodide in 4.5 ml dry tetrahydrofuran a solution of 0.50 g (0.91 mmol) 4-(2-hydroxy-ethoxy)-4'-o-tolyl-3,4,5,6-tetrahydro-2H-[1,2']bipyridinyl-5'-carboxylic acid (3,5-bis-trifluoromethyl-benzyl)-methyl-amide in 4.5 ml dry tetrahydrofuran was added dropwise at 0° C. under argon. After completed addition the reaction mixture was allowed to warm to room temperature. After 1 h 0.23 ml (1.1 mmol) (2-bromoethoxy)-tert-butyl-dimethylsilane were added dropwise. The reaction mixture was heated to 50° C. and stirred over night. After cooling to room temperature the reaction was quenched by addition of 5 ml water. The pH was adjusted to 2 by addition of 1 M aqueous hydrochloric acid solution. After 5 min. the mixture was basified with a saturated aqueous sodium carbonate solution and extracted with 3 portions of ethyl acetate. The combined organic extracts were washed with water, dried with sodium sulfate and concentrated to give 0.79 g of a yellow oil. Flash chromatography afforded 0.13 g (20%) of the title compound as a white solid.

MS m/e (%): 710 (M+H$^+$, 100).

Starting material (0.21 g, 42%) was recovered.

b) 4-(2-Hydroxy-ethoxy)-4'-o-tolyl-3,4,5,6-tetrahydro-2H-[1,2']bipyridinyl-5'-carbox (3,5-bis-trifluoromethyl-benzyl)-methyl-amide To a solution of 115 mg (0.162 mmol) (4-[2-(tert-butyl-dimethyl-silanyloxy)-ethoxy]-4'-o-tolyl-3,4,5,6-tetrahydro- 2H-[1,2']bipyridinyl-5'-carboxylic acid (3,5-bis-trifluoromethyl-benzyl)-methyl-amide in 3 ml dry tetrahydrofuran were added 0.17 ml (0.17 mmol) of a 1 M solution of tetrabutylammonium fluoride in tetrahydrofuran at room temperature under argon. After stirring over night the reaction mixture was diluted with ethyl acetate and washed with water. The layers were separated and the aqueous layer was extracted with two portions of ethyl acetate. The combined organic extracts were washed with two portions of water, dried with magnesium sulfate and concentrated to give 111 mg of a yellow oil. Flash chromatography afforded 59 mg (61%) of the title compound as a white solid.

MS m/e (%): 596 (M+H$^+$, 100).

EXAMPLE 5

(R)-N-(3,5-Bis-trifluoromethyl-benzyl)-6-(3-hydroxy-pyrrolidin-1-yl)-N-methyl-4-o-tolyl-nicotinamide The title compound was obtained as a colorless amorphous mass in comparable yield according to the procedure described above for the preparation of 4-hydroxy-4'-o-tolyl-3,4,5,6-tetrahydro-2H-[1,2']bipyridinyl-5'-carboxylic acid (3,5-bis-trifluoromethyl-benzyl)-methyl-amide using (R)-3-pyrrolidinol instead of 4-hydroxypiperidine.

MS m/e (%): 538 (M+H$^+$, 100).

EXAMPLE 6

4'-(2-Chloro-phenyl)-4-hydroxy-3,4,5,6-tetrahydro-2H-[1,2']bipyridinyl-5'-carboxylic aci (3,5-bis-trifluoromethyl-benzyl)-methyl-amide a) 4-Hydroxy-3,4,5,6-tetrahydro-2H-[1,2']bipyridinyl-5'-carboxylic acid methylamide A mixture of 8.51 g (49.9 mmol) 6-chloro-N-methyl-nicotinamide, 5.66 g (54.9 mmol) 4-hydroxypiperidine, 26.1 ml (150 mmol) N-ethyldiisopropylamine and 0.31 g (2.5 mmol) 4-(N,N-dimethylamino)-pyridine was heated at reflux over night. After cooling to room temperature the crude mixture was transferred to a flash chromatography column. Elution afforded 10.1 g (86.1%) of the title compound as a light yellow solid.

MS m/e (%): 236 (M+H$^+$, 100).

b) 4-(tert-Butyl-dimethyl-silanyloxy)-3,4,5,6-tetrahydro-2H-[1,2']bipyridinyl-5'-carboxylic acid methylamide A mixture of 10.1 g (42.9 mmol) 4-hydroxy-3,4,5,6-tetrahydro-2H-[1,2']bipyridinyl-5'-carboxylic acid methylamide, 8.0 g (52 mmol) tert-butyldimethylchlorosilane and 6.5 g (94 mmol) imidazole in 90 ml N,N-dimethylformamide was stirred at room temperature over night. The reaction was quenched with water. The resulting suspension was extracted with ethyl acetate. The organic extract was washed with 3 portions of water. The combined aqueous layers were extracted with 3 portions of dichloromethane. The combined organic extracts were dried with sodium sulfate, concentrated and dried in vacuo (0.5 mbar) at 80° C. Flash column chromatography afforded 14.6 g (97.3%) of the title compound as a light yellow solid.

MS m/e (%): 349 (M$^+$, 21).

c) 4-(tert-Butyl-dimethyl-silanyloxy)-4'-iodo-3,4,5,6-tetrahydro-2H-[1,2']bipyridinyl-5'-carboxylic acid methylamide To a solution of 500 mg (1.43 mmol) 4-(tert-butyl-dimethyl-silanyloxy)-3,4,5,6-tetrahydro-2H-[1,2'] bipyridinyl-5'-carboxylic acid methylamide, 1.7 ml (11 mmol) N,N,N',N'-tetramethyl-ethylenediamine and 1.0 ml (5.7 mmol) 2,2,6,6-tetramethylpiperidine in 9.5 ml dry tetrahydrofuran 7.2 ml (11 mmol) of a 1.6 M solution of n-butyllithium in hexanes were added dropwise during 10 min. at −78° C. under argon. The resulting solution was stirred at −78° C. for 30 min., warmed to −20° C. and stirred at this temperature for 3 h. After cooling the reaction mixture to −78° C. a solution of 2.92 g (11.5 mmol) iodine in 7 ml dry tetrahydrofuran was added dropwise under argon. The resulting suspension was kept at −78° C. for 2 h and subsequently allowed to warm to room temperature over 1 h. The suspension was poured into a solution of 12.4 g (50.0 mmol) sodium thiosulfate pentahydrate in 50 ml ice-water. The resulting yellow suspension was extracted with two 250-ml portions of tert-butyl methyl ether. The combined organic extracts were washed with 2 portions of a saturated aqueous ammonium chloride solution, dried with sodium sulfate and concentrated. Flash chromatography afforded 495 mg (72.8 %) of the title compound as an off-white amorphous mass.

MS m/e (%): 476 (M+H$^+$, 100).

d) 4-(tert-Butyl-dimethyl-silanyloxy)-4'-(2-chloro-phenyl)-3,4,5,6-tetrahydro-2H-[1,2']bipyridinyl-5'-carboxylic acid methylamide A mixture of 480 mg (1.01 mmol) 4-(tert-butyl-dimethyl-silanyloxy)-4'-iodo-3,4,5,6-tetrahydro-2H-[1,2']bipyridinyl-5'-carboxylic acid methylamide, 174 mg (1.11 mmol) 2-chlorophenylboronic acid, 6 ml dimethoxyethane and 1 ml of a 2 M aqueous solution of sodium carbonate was deoxygenated by three freeze-thaw cycles. After addition of 60 mg (0.052 mmol) tetrakis(triphenylphosphine)palladium(0) the reaction mixture was stirred at 90° C. for 3 h. Cooling to room temperature was followed by dilution with water and extraction with ethyl acetate. The organic extract was washed with saturated aqueous sodium carbonate and sodium chloride solutions, dried with sodium sulfate and concentrated. Column chromatography afforded 425 mg (91.5%) of the title compound as an off-white solid.

MS m/e (%):460 (M+H$^+$, 100).

e) 4-(tert-Butyl-dimethyl-silanyloxy)-4'-(2-chloro-phenyl)-3,4,5,6-tetrahydro-2H-[1,2']bipyridinyl-5'-carboxylic acid (3,5-bis-trifluoromethyl-benzyl)-methyl-amide The title compound was obtained as off-white foam in 49% yield according to the procedure described above for the preparation of N-(3,5-bis-trifluoromethyl-benzyl)-6-chloro-N-methyl-4-o-tolyl-nicotinamide using 4-(tert-butyl-dimethyl-silanyloxy)-4'-(2-chloro-phenyl)-3,4,5,6-tetrahydro-2H-[1,2']bipyridinyl-5'-carboxylic acid methylamide instead of 6-chloro-N-methyl-4-o-tolyl-nicotinamide.

MS m/e (%): 685 (M$^+$, 40).

f) 4'-(2-Chloro-phenyl)-4-hydroxy-3,4,5,6-tetrahydro-2H-[1,2']bipyridinyl-5'-carboxylic acid (3,5-bis-trifluoromethyl-benzyl)-methyl-amide The title compound was obtained as a white solid in 82% yield according to the procedure described above for the preparation of 4-(2-hydroxy-ethoxy)-4'-o-tolyl-3,4,5,6-tetrahydro-2H-[1,2']bipyridinyl-5'-carboxylic acid (3,5-bis-trifluoromethyl-benzyl)-methyl-amide using 4-(tert-butyl-dimethyl-silanyloxy)-4'-(2-chloro-phenyl)-3,4,5,6-tetrahydro-2H-[1,2']bipyridinyl-5'-carboxylic acid (3,5-bis-trifluoromethyl-benzyl)-methyl-amide instead of (4-[2-(tert-butyl-dimethyl-silanyloxy)-ethoxy]-4'-o-tolyl-3,4,5,6-tetrahydro-2H-[1,2']bipyridinyl-5'-carboxylic acid (3,5-bis-trifluoromethyl-benzyl)-methyl-amide.

MS m/e (%): 572 (M+H$^+$, 100).

EXAMPLE 7

2-(3,5-Bis-trifluoromethyl-phenyl)-N-[6-(2-hydroxy-ethylamino)-4-o-tolyl-pyridin-3-yl]-N-methyl-isobutyramide a) 4-(5-Nitro-2-pyridyl)-morpholine To a solution of 20 g (126 mmol) of 2-chloro-5-nitropyridine in 150 ml tetrahydrofuran were added dropwise 27 ml (315 mmol) morpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.3 g (quantitative) of the title compound as a yellow solid. M.p. 142–143° C.

b) 2,2-Dimethyl-N-(6-morpholin-4-yl-pyridin-3-yl)-propionamide

To a solution of 27.3 g (126 mmol) of 4-(5-nitro-2-pyridyl)-morpholine in 600 ml methanol were added 2.5 g of 10% of palladium on activated charcoal. The reaction mixture was hydrogenated (room temperature to ca. 45° C., 1 bar) until the theoretical amount of hydrogen was taken up (about 3 h). The catalyst was filtered off and was washed twice with 100 ml portions of methanol. The filtrate was evaporated in vacuo to give 22.6 g of a purple oil which consisted to ca. 95% of the desired aniline derivative according to analysis by thin layer chromatography.

This crude product was dissolved in a mixture of 240 ml tetrahydrofuran and 60 ml diethyl ether. After cooling to 0° C., 26 ml (189 mmol) of triethylamine were added in one portion. Stirring was continued while 23 g (189 mmol) of pivaloyl chloride were added dropwise within a period of 10 min. The ice bath was removed and the reaction mixture was stirred for 1 h at room temperature. Then, the solvent was removed in vacuo and the residue was suspended in 200 ml 1 N sodium bicarbonate solution. The product was extracted three times with 200 ml portions of dichloromethane, dried (sodium sulfate) and evaporated. Recrystallization of the solid residue from ethyl acetate/hexane 1:8 gave 28.6 g (86%) of the title compound as white crystals.

MS m/e (%): 264 (M+H$^+$, 100).

c) N-(4-Iodo-6-morpholin-4-yl-pyridin-3-yl)-2,2-dimethyl-propionamide

A solution of 28.4 g (108 mmol) 2,2-dimethyl-N-(6-morpholin-4-yl-pyridin-3-yl)-propionamide and 49 ml (324 mmol) N,N,N',N'-tetramethylethylenediamine under argon in 600 ml tetrahydrofuran was cooled in a dry ice bath to −78° C. Within 1 h, 202 ml (324 mmol) of a 1.6 N n-butyllithium solution in hexane were added dropwise. The reaction mixture was allowed to warm up to −35° C. overnight. After cooling again to −78° C., 37 g (146 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 15.6 g (37%) of the title compound as a light brown oil which crystallized upon standing at room temperature.

MS m/e (%): 389 (M$^+$, 71), 358 (25), 304 (43), 57 (100).

d) 2,2-Dimethyl-N-(6-morpholin-4-yl-4-o-tolyl-pyridin-3-yl)-propionamide

A mixture of 3.50 g (9.0 mmol) N-(4-iodo-6-morpholin-4-yl-pyridin-3-yl)-2,2-dimethyl-propionamide, 35 ml toluene, 18 ml 2 N sodium carbonate solution, 312 mg (0.27 mmol) tetrakis(triphenylphosphine)palladium(0) and 1.34 g (9.9 mmol) o-tolylboronic acid was heated under argon at 80° C. for 12 h. After cooling to room temperature, the aqueous phase was separated and washed twice with ethyl acetate. The combined organic layers were washed with 50 ml brine, dried (sodium sulfate) and evaporated. Purification by flash-chromatography gave 3.23 g (quantitative) of the title compound as a white foam.

MS m/e (%): 354 (M+H$^+$, 100).

e) 6-Morpholin-4-yl-4-o-tolyl-pyridin-3-ylamine

A suspension of 2.93 g (8.28 mmol) 2,2-dimethyl-N-(6-morpholin-4-yl-4-o-tolyl-pyridin-3-yl)-propionamide in 80 ml 3 N hydrochloric acid solution and 5 ml 1-propanol was heated to 90–95° C. overnight. The reaction mixture was cooled to room temperature, washed with three 20 ml portions diethyl ether and filtered over celite. The filtrate was diluted with 20 ml water and was adjusted to pH 7–8 by addition of 28% sodium hydroxide solution under ice cooling. The product was extracted with four 100 ml portions of dichloromethane. The combined organic layers were washed with 50 ml brine, dried (magnesium sulfate) and evaporated to give 2.31 g (quantitative) of the title compound as a white foam.

MS m/e (%): 269 (M$^+$, 100).

f) Methyl-(6-morpholin-4-yl-4-o-tolyl-pyridin-3-yl)-amine

A solution of 2.24 g (8.3 mmol) 6-morpholin-4-yl-4-o-tolyl-pyridin-3-ylamine in 17 ml trimethyl orthoformate and 3 drops trifluoroacetic acid was heated for 2 h at 130° C. The reaction mixture was evaporated and dried in vacuo for 30 min. The residual oil was dissolved in 5 ml tetrahydrofuran and was added dropwise under ice cooling to 630 mg (16.6 mmol) lithium aluminum hydride in 20 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 1.56 g (66%) of the title compound as a white foam.

MS m/e (%): 283 (M$^+$, 100).

g) 2-(3,5-Bis-trifluoromethyl-phenyl)-N-methyl-N-(6-mopholin-4-yl-4-o-tolyl-pyridin-3-yl)-isobutyramide A solution of 1.46 g (5.15 mmol) methyl-(6-morpholin-4-yl-4-o-tolyl-pyridin-3-yl)-amine and 1.32 ml (7.73 mmol) N-ethyldiisopropylamine in 15 ml dichloromethane was cooled in an ice bath and 1.8 g (5.67 mmol) 2-(3,5-bis-trifluoromethyl-phenyl)-2-methyl-propionyl chloride were added dropwise. The reaction mixture was warmed to 35–40° C. for 3 h, cooled to room temperature again and was stirred with 25 ml saturated sodium bicarbonate solution. The organic layer was separated and the aqueous phase was extracted with dichloromethane. The combined organic layers were dried (magnesium sulfate) and evaporated. The residue was purified by flash chromatography to give 2.9 g (quantitative) of the title compound as white crystals. M.p. 131–132° C.

h) 2-(3,5-Bis-trifluoromethyl-phenyl)-N-[6-(2-hydroxy-ethylamino)-4-o-tolyl-pyridin-3-yl]-N-methyl-isobutyramide A mixture of 1.0 g (1.76 mmol) 2-(3,5-bis-trifluoromethyl-phenyl)-N-methyl-N-(6-morpholin-4-yl-4-o-tolyl-pyridin-3-yl)-isobutyramide, 100 mg (0.48 mmol)

ruthenium(III)chloride hydrate, 832 mg (3.87 mmol) sodium periodate, 3.5 ml carbon tetrachloride, 3.5 ml acetonitrile and 5.3 ml water was stirred for 4 days at room temperature. Dichloromethane was added, the organic layer was separated, washed with sodium hydrogensulfite solution and filtered over celite. To the filtrate were added 10 ml 1 N potassium hydroxide solution and 20 ml methanol. After heating the mixture for 1 h at 40° C., the solvents were removed in vacuo and the residue was purified by flash-chromatography to give 352 mg (37%) of the title compound as light brown foam.

MS m/e (%): 540 (M+H$^+$, 100).

EXAMPLE 8

2-(3,5-Bis-trifluoromethyl-phenyl)-N-[4-(2-chloro-phenyl)-6-(2-hydroxy-ethylamino)-pyridin-3-yl]-N-methyl-isobutyramide The title compound was obtained as light brown foam in comparable yield according to the procedures described above for the preparation of 2-(3,5-bis-trifluoromethyl-phenyl)-N-[6-(2-hydroxy-ethylamino)-4-o-tolyl-pyridin-3-yl]-N-methyl-isobutyramide using 2-chloroboronic acid instead of o-tolylboronic acid in step d).

MS m/e (%): 560 (M+H$^+$, 100).

EXAMPLE 9

2-(3,5-Bis-trifluoromethyl-phenyl)-N-[6-(2,3-dihydro-[1,4]oxazin-4-yl)-4-o-tolyl-pyridin-3-yl]-N-methyl-isobutyramide a) 2-(3,5-Bis-trifluoromethyl-phenyl)-N-methyl-N-[6-(3-oxo-morpholin-4-yl)-4-o-tolyl-pyridin-3-yl]-isobutyramide To an ice-cooled suspension of 1.2 g (7.1 mmol) ruthenium(IV)oxide hydrate in a mixture of 50 ml carbon tetrachloride and 50 ml water were added 9.0 g (42 mmol) sodium periodate. After stirring for 30 min the organic layer was separated and the aqueous layer was extracted twice with 10-ml portions of carbon tetrachloride. The combined organic layers were filtered over celite, cooled to 0° C. and were added slowly to an ice-cooled solution of 2.0 g (3.54 mmol) 2-(3,5-bis-trifluoromethyl-phenyl)-N-methyl-N-(6-morpholin-4-yl-4-o-tolyl-pyridin-3-yl)-isobutyramide in 20 ml carbon tetrachloride. The mixture was stirred for additional 15 min at 0° C., was filtered over celite and was evaporated. The residue was purified by flash-chromatography and gave 704 mg (34%) of the title compound as colourless foam.

MS m/e (%): 580 (M+H$^+$, 100).

b) (RS)-2-(3.5-Bis-trifluoromethyl-phenyl)-N-[6-(3-hydroxy-morpholin-4-yl)-4-o-tolyl-pyridin-3-yl]-N-methyl-isobutyramide To an ice-cooled solution of 494 mg (0.852 mmol) 2-(3,5-bis-trifluoromethyl-phenyl)-N-methyl-N-[6-(3-oxo-morpholin-4-yl)-4-o-tolyl-pyridin-3-yl]-isobutyramide in 5 ml methanol and 5 ml tetrahydrofuran were added 635 mg (1.70 mmol) cerium(III)chloride heptahydrate. After stirring for 5 min, 64 mg (1.70 mmol) sodium borohydride were added in two portions within 2 min. After stirring for 3 h at 0° C., 1 ml acetone was added and stirring was continued for 10 min. The solvent was removed, the residue was re-dissolved in ethyl acetate and the organic phase was washed with saturated sodium carbonate solution, dried (magnesium sulfate) and evaporated. The crude material was purified by flash-chromatography to give 87 mg (16%) of the title compound as white crystals.

MS m/e (%): 582 (M+H$^+$, 100).

c) 2-(3,5-Bis-trifluoromethyl-phenyl)-N-[6-(2,3-dihydro-[1,4]oxazin-4-yl)-4-o-tolyl-pyridin-3-yl]-N-methyl-isobutyramide To a solution of 65 mg (0.11 mmol) (RS)-2-(3,5-bis-trifluoromethyl-phenyl)-N-[6-(3-hydroxy-morpholin-4-yl)-4-o-tolyl-pyridin-3-yl]-N-methyl-isobutyramide in 2 ml chloroform were added a few drops of a 2.3 N hydrochloric acid solution in diethyl ether. After stirring at room temperature for 2 h, the organic layer was washed with saturated sodium carbonate solution, dried (magnesium sulfate) and evaporated. The residue was purified by flash-chromatography to give 47 mg (75%) of the title compound as white foam.

MS m/e (%): 564 (M+H$^+$, 100).

EXAMPLE 10

N-(6-Acetylamino-4-o-tolyl-pyridin-3-yl)-2-(3,5-bis-trifluoromethyl-phenyl)-N-methyl-isobutyramide a) N2-Benzyl-N5-methyl-4-o-tolyl-pyridine-2,5-diamine The title compound was prepared following the procedures described above for the synthesis of methyl-(6-morpholin-4-yl-4-o-tolyl-pyridin-3-yl)-amine.

MS m/e (%): 304 (M+H$^+$, 100).

b) Benzyl-(5-methylamino-4-o-tolyl-pyridin-2-yl)-carbamic acid benzyl ester

To a solution of 2.03 g (6.7 mmol) N2-benzyl-N5-methyl-4-o-tolyl-pyridine-2,5-diamine in 100 ml dichloromethane and 40 ml N-ethyldiisopropylamine a solution of 2.1 ml (14.09 mmol) benzyl chloroformate in 50 ml dichloromethane was added dropwise at 0° C. After stirring for 2 h at room temperature the reaction mixture was washed with water (2×50 ml), brine (50 ml), dried (magnesium sulfate) and evaporated. Chromatography of the residue afforded 2.36 g (80%) of the title compound as light brown crystals. M.p. 110–112° C.

MS m/e (%): 438 (M+H$^+$, 100).

c) Benzyl-(5-{[2-(3,5-bis-trifluoromethyl-phenyl)-2-methyl-propionyl]-methyl-amino}-4-o-tolyl-pyridin-2-yl)-carbamic acid benzyl ester To a solution of 1.075 g (2.5 mmol) benzyl-(5-methylamino-4-o-tolyl-pyridin-2-yl)-carbamic acid benzyl ester in 10 ml dichloromethane and 1 ml N-ethyldiisopropylamine was added dropwise at 0° C. a solution of 1.15 g (3.5 mmol) 2-(3,5-bis-trifluoromethyl-phenyl)-2-methyl-propionic acid chloride in 2 ml dichloromethane and the mixture was stirred for 3 h at room temperature. The solution was washed with water (20 ml), saturated aqueous sodium hydrogencarbonate solution (20 ml) and brine (20 ml), dried (magnesium sulfate) and evaporated. Chromatography of the residue afforded 1.15 g (62%) of the title compound as a yellow oil.

MS m/e (%): 720 (M+H$^{30}$, 100).

d) N-(6-Benzylamino-4-o-tolyl-pyridin-3-yl)-2-(3,5-bis-trifluoromethyl-phenyl)-N-methyl-isobutyramide To a solution of 973 mg (1.35 mmol) benzyl-(5-{[2-(3, 5-bis-trifluoromethyl-phenyl)-2-methyl-propionyl]-methyl-amino}-4-o-tolyl-pyridin-2-yl)-carbamic acid benzyl ester in 13 ml methanol and 1 ml N,N-dimethylformamide was added 40 mg 10% palladium on activated charcoal and the mixture was hydrogenated (room temperature, 1 bar) for 1 h. Filtration of the catalyst and evaporation of the filtrate afforded 795 mg (quantitative) of the title compound as a yellow oil.

MS m/e (%): 586 (M+H$^+$, 100).

e) N-(6-Amino-4-o-tolyl-pyridin-3-yl)-2-(3,5-bis-trifluoromethyl-phenyl)-N-methyl-isobutyramide A solution of 750 mg (1.28 mmol) N-(6-benzylamino-4-o-tolyl-pyridin-3-yl)-2-(3,5-bis-trifluoromethyl-phenyl)-N- methyl-isobutyramide in 25 ml of a 5 N solution of hydrochloric acid in ethanol was evaporated to dryness and the residue was dissolved in 30 ml methanol and hydrogenated in the presence of 60 mg 10% palladium on activated charcoal (room temperature, 10 bar) for 20 h. After filtration of the catalyst and evaporation of the solvent the residue was dissolved in 30 ml ethyl acetate, washed twice with saturated aqueous sodium hydrogencarbonate solution and dried (magnesium sulfate). Evaporation of the solution afforded 514 mg (81%) of the title compound as light brown crystals.

MS m/e (%): 496 (M+H$^+$, 100).

f) N-(6-Acetylamino-4-o-tolyl-pyridin-3-yl)-2-(3,5-bis-trifluoromethyl-phenyl)-N-methyl-isobutyramide To a solution of 100 mg (0.20 mmol) N-(6-amino-4-o-tolyl-pyridin-3-yl)-2-(3,5-bis-trifluoromethyl -phenyl)-N-methyl-isobutyramide in 3 ml dichloromethane were added 27 mg (0.21 mmol) N-ethyldiisopropylamine and 70 mg (0.69 mmol) acetic anhydride. After stirring overnight, the solvent was evaporated and the residue was purified by flash-chromatography to give 100 mg (92%) of the title compound as white solid.

MS m/e (%): 537 (M$^+$, 68), 282 (100).

EXAMPLE 11

N-[6-(Acetyl-methyl-amino)-4-o-tolyl-pyridin-3-yl]-2-(3,5-bis-trifluoromethyl-phenyl)-N-methyl-isobutyramide To a solution of 60 mg (0.11 mmol) N-(6-acetylamino-4-o-tolyl-pyridin-3-yl)-2-(3,5-bis-trifluoromethyl-phenyl)-N-methyl-isobutyramide in 2 ml tetrahydrofuran at room temperature under argon were added dropwise 0.13 ml (0.12 mmol) of a 1 M solution of potassium hexamethyldisilazide in tetrahydrofuran. Stirring was continued for 1 h at room temperature and 17 mg (0.12 mmol) methyl iodide were added. After stirring overnight, the solvent was evaporated and the residue was purified by flash-chromatography to give 40 mg (65%) of the title compound as white foam.

MS m/e (%): 574 (M+Na$^+$, 17), 552 (M+H$^+$, 100).

EXAMPLE 12

Cyclopropanecarboxylic Acid (5-{[2-(3,5-bis-trifluoromethyl-phenyl)-2-methyl-propionyl]-methyl-amino}-4-o-tolyl-pyridin-2-yl)-amide To a solution of 100 mg (0.20 mmol) N-(6-amino-4-o-tolyl-pyridin-3-yl)-2-(3,5-bis-trifluoromethyl-phenyl)-N-methyl-isobutyramide in 3 ml dichloromethane were added 2 ml pyridine and 23 mg (0.22 mmol) cyclopropanecarboxylic acid chloride at 0° C. After stirring for 2 days at room temperature, the solvent was removed in vacuo and the residue was purified by flash-chromatography to give 61 mg (54%) of the title compound as white solid.

MS m/e (%): 586 (M+Na$^+$, 25), 564 (M+H$^+$, 100).

EXAMPLE 13

Cyclopropanecarboxylic acid (5-{[2-(3,5-bis-trifluoromethyl-phenyl)-2-methyl-propionyl]-methyl-amino}-4-o-tolyl-pyridin-2-yl)-methyl-amide The title compound was prepared as a white foam in comparable yield according to the procedure described above for the preparation of N-[6-(acetyl-methyl-amino)-4-o-tolyl-pyridin-3-yl]-2-(3,5-bis-trifluoromethyl-phenyl)-N-methyl-isobutyramide using cyclopropanecarboxylic acid (5-{[2-(3,5-bis-trifluoromethyl-phenyl)-2-methyl-propionyl]-methyl-amino}-4-o-tolyl-pyridin-2-yl)-amide instead of N-(6-acetylamino-4-o-tolyl-pyridin-3-yl)-2-(3,5-bis-trifluoromethyl-phenyl)-N-methyl-isobutyramide.

MS m/e (%): 600 (M+Na$^+$, 22), 578 (M+H$^+$, 100).

EXAMPLE 14

2-(3,5-Bis-trifluoromethyl-phenyl)-N-(6-imidazol-1-yl-4-o-tolyl-pyridin-3-yl)-N-methyl-isobutyramide a) 6-Imidazol-1-yl-4-o-tolyl-pyridin-3-ylamine The title compound was obtained as light brown foam according to the procedures described above for the preparation of 6-morpholin-4-yl-4-o-tolyl-pyridin-3-ylamine (Example 7, step e)) using imidazole instead of morpholine in step a).

MS m/e (%): 251 (M+H$^+$, 100).

b) 2-(3,5-Bis-trifluoromethyl-phenyl)-N-(6-imidazol-1-yl-4-o-tolyl-pyridin-3-yl)-isobutyramide The title compound was obtained as yellow crystals according to the procedure described above for the preparation of 2-(3,5-bis-trifluoromethyl-phenyl)-N-methyl-N-(6-morpholin-4-yl-4-o-tolyl-pyridin-3-yl)-isobutyramide (Example 7, step g)) using 6-imidazol-1-yl-4-o-tolyl-pyridin-3-ylamine instead of methyl-(6-morpholin-4-yl-4-o-tolyl-pyridin-3-yl)-amine.

MS m/e (%): 532 (M$^+$, 100).

c) 2-(3 5-Bis-trifluoromethyl-phenyl)-N-(6-imidazol-1-yl-4-o-tolyl-pyridin-3-yl)-N-methyl-isobutyramide The title compound was obtained as white crystals according to the procedure described above for the preparation of N-(3,5-bis-trifluoromethyl-benzyl)-6-chloro-N-methyl-4-o-tolyl-nicotinamide (Example 1, step c)) using 2-(3,5-bis-trifluoromethyl-phenyl)-N-(6-imidazol-1-yl-4-o-tolyl-pyridin-3-yl)-isobutyramide instead of 6-chloro-N-methyl-4-o-tolyl-nicotinamide and methyl iodide instead of 3,5-bis(trifluoromethyl)benzyl bromide.

MS m/e (%): 547 (M+H$^+$, 100).

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound, N-(3,5-bis-trifluoromethyl-benzyl)-N-methyl-4-o-tolyl-6-[1,2,4]triazol-1-yl-nicotinamide.

2. A compound, 2-(3,5-bis-trifluoromethyl-phenyl)-N-[6-(2,3-dihydro-[1,4]oxazin-4-yl)-4-o-tolyl-pyridin-3-yl]-N-methyl-isobutyramide.

3. A compound, 2-(3,5-bis-trifluoromethyl-phenyl)-N-(6-imidazol-1-yl-4-o-tolyl-pyridin-3-yl)-N-methyl-isobutyramide.

* * * * *